United States Patent
Carter

(10) Patent No.: US 9,572,906 B2
(45) Date of Patent: Feb. 21, 2017

(54) COMPOSITION FOR REDUCING TOILET ODOR CONTAINING POLYPROPYLENE GLYCOL AS A REACTIVE GAS BARRIER

(71) Applicant: KENDALL MOULDING & FRAMES, INC., Huntsville, AL (US)

(72) Inventor: Daniel C. Carter, Fayetteville, TN (US)

(73) Assignee: BINFORD HOLDINGS, LLC, Huntsville, AL (US)

( * ) Notice: Subject to any disclaimer, the term of this patent is extended or adjusted under 35 U.S.C. 154(b) by 0 days.

(21) Appl. No.: 13/743,431

(22) Filed: Jan. 17, 2013

(65) Prior Publication Data

US 2014/0199257 A1 Jul. 17, 2014

(51) Int. Cl.
| | |
|---|---|
| *A61L 11/00* | (2006.01) |
| *A61L 9/01* | (2006.01) |
| *C11D 3/37* | (2006.01) |
| *C11D 3/50* | (2006.01) |
| *C11D 7/26* | (2006.01) |

(52) U.S. Cl.
CPC .................. *A61L 11/00* (2013.01); *A61L 9/01* (2013.01); *C11D 3/3707* (2013.01); *C11D 3/50* (2013.01); *C11D 7/261* (2013.01)

(58) Field of Classification Search
None
See application file for complete search history.

(56) References Cited

U.S. PATENT DOCUMENTS

| | | | | |
|---|---|---|---|---|
| 3,436,278 | A | * | 4/1969 | Poliak ................. B23K 35/3612 106/287.24 |
| 4,235,743 | A | * | 11/1980 | Canevari .................. B01J 19/16 252/382 |
| 4,666,671 | A | | 5/1987 | Purzycki et al. |
| 4,722,801 | A | | 2/1988 | Bunczk et al. |
| 4,911,858 | A | | 3/1990 | Bunczk et al. |
| 5,009,887 | A | | 4/1991 | Iwahashi |
| 5,072,020 | A | * | 12/1991 | Speranza et al. ................ 560/25 |
| 5,307,525 | A | | 5/1994 | O'Brien |
| 5,449,473 | A | | 9/1995 | Bunczk et al. |
| 5,707,961 | A | | 1/1998 | Bajgrowicz et al. |
| 5,709,872 | A | | 1/1998 | Van Rees |
| 5,958,334 | A | | 9/1999 | Haddon |
| 6,066,293 | A | * | 5/2000 | Van Rees ................ A01N 57/12 4/222 |
| 6,245,291 | B1 | | 6/2001 | Van Rees |
| 7,449,441 | B2 | | 11/2008 | Edwards et al. |
| 7,998,921 | B2 | | 8/2011 | Edwards et al. |
| 8,220,497 | B1 | | 7/2012 | Guarascio |
| 2003/0008792 | A1 | | 1/2003 | Shaukat et al. |
| 2003/0068295 | A1 | | 4/2003 | Rohde et al. |
| 2007/0152190 | A1 | * | 7/2007 | Borish ..................... B01J 19/16 252/382 |
| 2009/0238787 | A1 | | 9/2009 | Finke et al. |
| 2010/0235975 | A1 | | 9/2010 | Cheung et al. |
| 2011/0209276 | A1 | | 9/2011 | Lu et al. |
| 2011/0223059 | A1 | | 9/2011 | Lu et al. |

OTHER PUBLICATIONS

Ralston et al., Foaming of polypropylene glycols and glycol/MIBC mixtures, Mineral Engineering, 2005, vol. 18, pp. 179-188.*
Dow, Polyglycolether product monograph P-1000E.*
Bayer, Polyprylene glycol product PPG-1000, PPG-2000, PPG-3000, PPG-4000.*
White et al. (Mosquito control with monomolecular organic surface films: I-selection of optimum film-forming agents, Mosquito News, 1977, vol. 37, p. 344-348).*
International Search Report and Written Opinion dated May 6, 2014 in corresponding International Application No. PCT/US2014/012099.

* cited by examiner

*Primary Examiner* — Bethany Barham
*Assistant Examiner* — Ping Cao
(74) *Attorney, Agent, or Firm* — B. Aaron Schulman, Esq.; Stites & Harbison, PLLC.

(57) ABSTRACT

A method and composition is provided that aids in the reduction of objectionable volatile odors when a few drops are placed in the toilet prior to use. In one embodiment, the composition contains a high molecular weight polypropylene glycol (PPG) together with a dispersing agent to create an instantaneous multifunctional surface barrier of the polypropylene glycol/isopropanol mixture across the water surface. The composition may also optionally include one or more essential oils, fragrances or colorants.

9 Claims, No Drawings

COMPOSITION FOR REDUCING TOILET ODOR CONTAINING POLYPROPYLENE GLYCOL AS A REACTIVE GAS BARRIER

FIELD OF THE INVENTION

This application relates to methods and compositions for reducing toilet odors and other odors associated with standing water.

BACKGROUND OF THE INVENTION

In humans, stool odor is produced by the enzymatic activity of the natural bacterial flora in the intestinal tract. Bacteria live symbiotically in the gut and aid in the digestion of a variety of important nutrients. The odor producing metabolic products of this bacteria-based enzymatic digestion include a variety of low molecular weight organics, such as indoles, skatole and a variety of thiols. The principal, causing flatulence, and the most volatile of these metabolic products is hydrogen sulfide gas which is also highly chemically reactive, e.g., with alcohols. The bulk of the other objectionable odorants, despite the varying nature of chemical structure, are hydrophobic in nature, making them amenable to entrapment in a suitable hydrophobic surface matrix.

PRIOR ART

There are a variety of products recently marketed for personal use in the reduction or elimination of toilet odor. Some of these are disclosed in patent references including US 2003/0008792 (Shaukat et al.), US 2003/0068295 (Rohde et al.), U.S. Pat. No. 4,722,801 (Bunczk, et al.), U.S. Pat. No. 7,998,921 (Edwards, et al.) and U.S. Pat. No. 8,220,497 (Guarasclo, D.), all of said patent documents incorporated herein by reference. These are generally point of use personal products which are administered by placing a few drops of a solution to the surface water of the toilet prior to use. Prior art examples currently in use have incorporated what appear to be three potential mechanisms:

(1) incorporation of a masking agent. The primary active ingredient of these products is simply a strong fragrance or perfume. A product example which uses an essential oil for these purposes would be "Just a Drop" manufactured by Prelam Enterprises Ltd. of Moncton, New Brunswick, Canada, which is listed on the label as having the following ingredients, plant extract, disinfectant, and perfume.

(2) creation of a surface barrier. Surface barriers can be created any of the following means, by use of an emulsion, a lipid matrix or use of a more complex organic. An example of a lipid based buoyant micro emulsion is a product manufactured by S2 Synergy, LLC, Addison, Tex., and marketed as Poo Pourri. Examples of the use of a complex organic as a surface barrier are: a) a commercial product known as "Powerful One-Drop" produced or marketed by Kobayashi Pharmaceutical Co. Ltd. Of Japan, per the label is comprised of fragrances, plant extract, and glycol ether (dipropylene glycol monoether) and b) that described by Edwards, et al., incorporated herein by reference, which contains from 60 to about 70% diethylene glycol mono-ethyl ether (($CH_2OHCH_2OCH_2CH_2OC_2H_5$).

(3) deliberate addition of active chemical reactants to neutralize odorants, such as hydrogen sulfide; the deliberate addition of significant quantities of a reactive alcohol, is considered new and part of this work.

This invention incorporates all three mechanisms, but does NOT use glycol ether, diethylene glycol mono-ethyl ether, dipropylene glycol, low molecular weight PPGs with an average molecular weight less that 1000 or buoyant micro emulsions.

None of the aforementioned products, however, have utilized polypropylene glycol (PPG) as an active surface agent. The incorporation of small amounts of PPG in toilet odor reducing substances has been limited to either use as a plasticizer or within an undefined complex mixture associated with the solid cake formation for passive devices used in the deodorization of urinals and toilets, and/or to use propylene glycol to affect melting point of urinal deodorant gels. For example, Bunczk et al., incorporated PPG MW 485 (10% or less) or 1000 (6% or less) in the formulation of solid cakes to create a lavatory cleansing block.

In a completely different application Guarasclo, cited herein by reference, describes a use of polyethylene glycol (PEG)/water mixtures for use in drain traps in buildings to slow evaporation rates and/or prevent freezing of the drain in unoccupied buildings. PEG mixes with water to form a solution that limits evaporation (by hygroscopic action rather than surface film) and prevents freezing in drain traps, having the advantage of lowering maintenance and delaying occurrences where sewer gas may enter buildings when these drain traps sit unused for long periods of time. Guarasclo also claims the general use of glycols, including PPG for the same purpose. However, and quite importantly, he does not mention the MW of the PPG being used, and teaches the water mixture of the PEG and other members of the glycol family as general statements without regard to the widely divergent chemical properties of these two glycol families. For example, PPG in MW 2000 is a more hydrophobic substance that is only sparingly soluble with water, the vast majority remains un-dissolved and floats on the water surface. It is therefore apparent to one skilled in the art that Guarasclo is either referring to a low molecular weight PPGs or simply propylene glycol, which are more generally miscible with water and therefore have hydrogen bonding properties similar to PEG (which is completely misc. in water under a wide MW weight range) or Guarasclo is unaware of the difference chemical properties of higher molecular weight PPGs. In addition, the use of PPG described by Guarasclo as a water mixture is contrary to the disclosed invention here. Unlike the present invention, his application would require large amounts of solution to fill the trap, nor does he teach the use of high MW PPGs as a surface film agent. Further, the addition of a dispersing agent, such as isopropanol, vide infra, is not taught, without which the current invention described herein would not be function/practical. Therefore it is clear the current application of PPG is not anticipated by Guarasclo.

SUMMARY OF THE INVENTION

A method of reducing or eliminating toilet odor or odor arising from other water surfaces is provided which comprises adding, placing or otherwise providing to a location wherein said odor may arise or be present a composition which comprises an active surface barrier agent of high molecular weight polypropylene glycol and a dispersal agent for the high molecular weight polypropylene glycol sufficient to cause the polypropylene glycol to instantaneous spread across the surface. Other features and advantages of the methods and compositions in accordance with the present invention are set forth hereinbelow.

DESCRIPTION OF THE PREFERRED EMBODIMENTS

This invention describes the use of PPG (polypropylene glycol) as an effective multifunctional surface agent to block, trap or react with volatile offensive toilet odors. Used alone, PPG forms localized thick highly viscous oil-like drops on the surface of water which do not spread evenly over the entire surface. High molecular weight PPG must be thinned by an appropriate dispersal agent to form a suitable rapidly forming barrier which can be achieved using small quantities (a few drops) of solution. It is the combination of PPG with an appropriate dispersal agent which creates a unique, stable functional base for the reduction of toilet odor with many desirable attributes. Some of the attributes include the ability to blend homogeneous mixtures with essential fragrant oils, perfumes, lipids, colorants, etc. to produce the desired combination for a specific consumer or institutional market. Preferably, the selection of a dispersal agent will also serve other functions, such as acting as an antimicrobial/preservative, or to enhance the barrier function, (improve the barriers ability to trap indoles, skatoles, etc.) and/or to serve as an additional reactant with hydrogen sulfide. Certain additives act as excellent dispersal agents as well, creating the rapid formation of an evenly dispersed film over the surface of water. Isopropyl alcohol is one such dispersal agent of choice for PPG, having also antibacterial and odorant reactant properties. In addition to creating the hydrophobic barrier, the alcohol moiety of PPG also serves as a potential reactant to hydrogen sulfide. Thus PPG and the PPG/isopropanol mixture is a multifunctional surface barrier (vs. just a lipid or lipid emulsion barrier) with functions in all three odor reducing mechanisms previously described in the Prior Art section. The chemical reactivity of alcohols with $H_2S$, the principal volatile odorant, for example, increases from primary to secondary to tertiary alcohols. The base solution of PPG and isopropyl alcohol has the added advantage that it is readily mixable with essential oils and other hydrophobic compounds which may be used to both produce a pleasant fragrance and enhance the hydrophobicity of the barrier function. It is therefore an object of the present invention to provide a composition of PPG when used together with isopropyl alcohol (or other desirable dispersing agent), may be used in essentially a drop wise manner to virtually instantaneously spread across the water surface of the toilet to form the desired volatile entrapment barrier. The balance of the ingredients being one or more stabilizers, one or more fragrances, one or more dispersing agents and one or more odor reacting chemicals.

In the preferred embodiment, a method of reducing or eliminating toilet odor or odor arising from other water surfaces is provided comprising providing to a location wherein said odor may arise or be present a composition which comprises an active surface barrier agent of high molecular weight polypropylene glycol and a dispersal agent for the high molecular weight polypropylene glycol sufficient to cause the polypropylene glycol to instantaneously spread across the surface. In the composition utilized in this method, the concentration of polypropylene glycol may be in the range of 10% to 90%, and preferably may be more than 20%. In addition, the average molecular weight of the polypropylene glycol is greater than 1000 MW, and can preferably be about 2000, 2700 or 4000. In one embodiment, the dispersal agent may be isopropyl alcohol, but the dispersal agent may be any suitable agent for the high molecular weight polypropylene glycol sufficient to cause the polypropylene glycol to instantaneously spread across the surface. The dispersal agent may also have a concentration range of 10 to 90%. The composition used in the above method may also further comprises essential oils for fragrance and/or surface barrier enhancement, and in addition can optionally contain an esthetic colorant or dye.

In one suitable method in accordance with the invention, the composition may be added in any suitable form, such as by dropper bottle, solid gel cake, or semi-automated device. In general, in the method of the invention, the composition may be placed in, on or adjacent to a toilet, or in, on or adjacent to the water surface in drain traps, airlocks or septic systems of buildings and recreational vehicles.

In the present invention, the preferred composition thus comprises an active surface barrier agent of high molecular weight polypropylene glycol and a dispersal agent for the high molecular weight polypropylene glycol sufficient to cause the polypropylene glycol to instantaneously spread across the surface. Such a composition will be suitable for reducing or eliminating odor such as toilet odor or other odors that may arise in, on or adjacent to the toilet or to the water surface in drain traps, airlocks or septic systems of buildings, recreational vehicles and other locations. This composition may also include essential oils for fragrance and/or surface barrier enhancement or an esthetic colorant or dye.

Method of use: The composition may be added using a dropper bottle to administer a few drops to the water surface prior to use of the toilet, or by any one of a number of automatic systems which inject a solution onto the surface of the water. In additional to personal use and household applications, there are also institutional applications. Institutional settings such as airports, hospitals and nursing homes can experience significant odor related issues due to the number of people, close proximity of the patients, the use bed pans and of shared facilities, etc. The invention described herein is an inexpensive and effective means to control embarrassing and objectionable odors in such situations. Additional applications of this invention would include use as a drain deodorizing agent and for use in the septic systems of recreational vehicles.

The following examples are for the purpose of illustration only and are in no way to be considered as limiting. Various changes and modifications in the formulation disclosed herein will occur to those skilled in the art and to the extent that such changes and modifications are embraced by the claims, they are to be understood as constituting part of the present invention.

One preferred embodiment of the invention would include a mixture of PPG/isopropanol/essential oil (fragrant oil) in the ratio of 5:5:3. The ratios of the ingredients can be varied, but it is desirable to have the PPG concentration in the final mixture, not less than 20% with those having greater than 30% by volume being more desirable.

Example 1

A mixture containing polypropylene glycol/isopropanol/essential oil (fragrance) in the following ratios by volume: 5:5:2 was prepared wherein the PPG has an average MW of 2000 (CAS No. 25323-30-2), the isopropyl alcohol is isopropanol (CAS No. 67-63-0 90% v/v), and the essential oil is purified from cedar wood (*Cupressus funebris*). This mixture was suitable to reduce and/or eliminate odors.

What is claimed is:

1. A method of reducing or eliminating toilet odor or other odor arising from a water surface comprising applying dropwise to said water surface a liquid composition comprising 20% to 90% by volume of a polypropylene glycol liquid active surface barrier agent having an average molecular weight from about 2000 Da to about 2700 Da, and an isopropyl alcohol dispersal agent in an amount that is sufficient to cause the polypropylene glycol to spread across the water surface and form an active surface barrier against said odors.

2. The method according to claim 1 wherein the polypropylene glycol has a concentration of at least 30% by volume.

3. The method according to claim 1 wherein the isopropyl alcohol has a concentration of at least 10% by volume.

4. The method according to claim 1 wherein the composition contains an aesthetic colorant or dye.

5. The method according to claim 1 wherein the composition is added by dropper bottle or semi-automated device.

6. The method according to claim 1 wherein the composition is placed in, on or adjacent to a toilet, or in, on or adjacent to the water surface in drain traps, airlocks or septic systems of buildings or recreational vehicles.

7. The method according to claim 1 wherein the composition further comprises essential oils for fragrance and/or surface barrier enhancement.

8. The method according to claim 7 wherein the ration of polypropylene glycol to isopropyl alcohol to essential oils is 5:5:3.

9. A method of reducing or eliminating toilet odor or other odor arising from a water surface comprising applying to said water surface a liquid composition comprising 20% to 90% by volume of a polypropylene glycol liquid active surface barrier agent having an average molecular weight from about 2000 Da to about 2700 Da, and an isopropyl alcohol dispersal agent in an amount that is sufficient to cause the polypropylene glycol to spread across the water surface and form an active surface barrier against said odors, wherein the isopropyl alcohol has a concentration of at least 10% by volume.

* * * * *